United States Patent [19]

Torii et al.

[11] Patent Number: 5,693,792

[45] Date of Patent: Dec. 2, 1997

[54] β-LACTAM AND CEPHEM COMPOUNDS AND PROCESSES FOR THEIR PRODUCTION

[75] Inventors: Shigeru Torii; Hideo Tanaka, both of Okayama; Mitio Sasaoka; Takashi Shiroi, both of Tokushima; Yutaka Kameyama, Okayama, all of Japan

[73] Assignee: Otsuga Kagaku Kabushiki Kaisha, Osaka-shi, Japan

[21] Appl. No.: 515,166

[22] Filed: Aug. 15, 1995

Related U.S. Application Data

[62] Division of Ser. No. 129,130, filed as PCT/JP93/00131, Feb. 3, 1993, Pat. No. 5,470,972.

[30] Foreign Application Priority Data

Feb. 18, 1992 [JP] Japan ..................................... 4-30310
Feb. 18, 1992 [JP] Japan ..................................... 4-30311

[51] Int. Cl.[6] .................. C07D 205/09; C07D 205/095; C07D 501/22; C07D 501/02
[52] U.S. Cl. .......................................................... 540/358
[58] Field of Search .............................................. 540/358

[56] References Cited

U.S. PATENT DOCUMENTS

| | | | |
|---|---|---|---|
| 4,066,641 | 1/1978 | Hamashima | 540/358 |
| 4,463,172 | 7/1984 | Horii et al. | 540/218 |
| 4,798,890 | 1/1989 | Torii et al. | 540/358 |
| 5,077,286 | 12/1991 | Bissolino et al. | 540/221 |
| 5,132,301 | 7/1992 | Doherty et al. | 540/221 |
| 5,162,521 | 11/1992 | Farema | 540/358 |

OTHER PUBLICATIONS

Tanaka I, SYNLETT 1992, 351.
Tanaka II, SYNLETT 1992, 878.

*Primary Examiner*—Mark L. Berch
*Attorney, Agent, or Firm*—Armstrong, Westerman, Hattori, McLeland & Naughton

[57] ABSTRACT

The object of the invention is to provide a β-lactam compound and a 2-substituted methyl-3-cephem compound, both of which are of value as intermediates for the synthesis of cephem antibiotics.

The β-lactam compound of the invention may be represented by the general formula

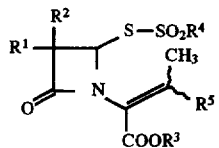

wherein $R^1$ represents a protected amino group, for instance; $R^2$ represents hydrogen, for instance; $R^3$ represents hydrogen or a carboxy-protecting group; $R^4$ represents an aryl group which may be substituted; $R^5$ represents an alkenyl group which may be substituted, for instance. The 2-substituted methyl-3-cephem compound of the invention may be represented by the general formula

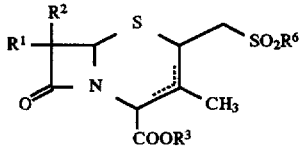

wherein $R^1$, $R^2$ and $R^3$ are as defined above; $R^6$ represents an aryl group which may be substituted.

1 Claim, No Drawings

β-LACTAM AND CEPHEM COMPOUNDS AND PROCESSES FOR THEIR PRODUCTION

This is a division of application Ser. No. 08/129,130 filed Oct. 14, 1993, now U.S. Pat. No. 5,470,972, which is a § 371 of application PCT/JP93/00131 filed Feb. 3, 1993.

TECHNICAL FIELD

The present invention relates to novel β-lactam compounds and cephem compounds and to processes for their production.

DISCLOSURE OF INVENTION

The β-lactam compounds and 2-substituted methyl-3-cephem compounds according to the present invention are novel compounds not heretofore described in the literature and are of use as intermediates for the synthesis of 2-exomethylenecephem derivatives. 2-Exomethylenecephem derivatives are not only compounds having antibacterial activity of their own [Journal of Medical Chemistry 14(5), 420 (1971)] but also are compounds of value as intermediates of various cephem compounds [do. 14(5), 426 (1971), do. 22(6), 743 (1979) and Tetrahedron Letters 26, 2413 (1973)].

It is an object of the invention to provide a β-lactam compound which is an important intermediate for the synthesis of 2-exomethylenecephem compounds.

Another object of the invention is to provide a process for producing said β-lactam compound.

It is still another object of the invention to provide a 2-substituted methyl-3-cephem compound which is an intermediate of value for the synthesis of 2-exomethylenecephem derivatives.

It is a further object of the invention to provide a process for producing said cephem compound.

Another yet object of the invention is to provide a process for producing a 2-exomethylenecephem compound from said 2-substituted methyl-3-cephem compound.

The β-lactam compound of the invention is a novel class of compounds which can be represented by the following general formula (1).

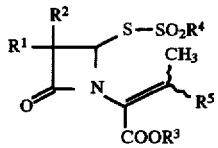

wherein $R^1$ represents a hydrogen atom, a halogen atom, an amino group or a protected amino group; $R^2$ represents a hydrogen atom, a halogen atom, a lower alkoxy group, a lower acyl group, a lower alkyl group, a lower alkyl group substituted by a hydroxyl or protected hydroxyl group, a hydroxyl group or a protected hydroxyl group; $R^1$ and $R^2$ may jointly represent a group of =O; $R^3$ represents a hydrogen atom or a carboxy-protecting group; $R^4$ represents an aryl group which may be substituted; $R^5$ represents a $C_{2-6}$ alkyl group, an alkenyl group which may be substituted, an alkynyl group which may be substituted, an aryl group which may be substituted or a nitrogen-containing heteroaromatic group which may be substituted.

The 2-substituted methyl-3-cephem compound of the invention is a novel compound that has not been described in the literature and can be represented by the following general formula (2).

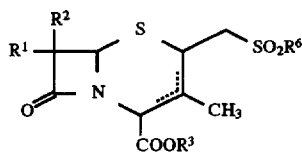

wherein $R^1$, $R^2$ and $R^3$ are as defined above; $R^6$ represents an aryl group which may be substituted.

The respective groups mentioned in this specification have the specific meanings defined hereunder. Unless otherwise indicated, the halogen atom means any of fluorine, chlorine, bromine, iodine, etc. The lower alkyl group means a straight- or branched-chain $C_1$–$C_4$ alkyl group such as methyl, ethyl, n-propyl, isopropyl, n-butyl, isobutyl, sec-butyl, tert-butyl, etc. The aryl group means any of phenyl, naphthyl and so on.

The protected amino group $R^1$ includes, among others, phenoxyacetamido, p-methylphenoxyacetamido, p-methoxyphenoxyacetamido, p-chlorophenoxyacetamido, p-bromophenoxyacetamido, phenylacetamido, p-methylphenylacetamido, p-methoxyphenylacetamido, p-chlorophenylacetamido, p-bromophenylacetamido, phenylmonochloroacetamido, phenyldichloroacetamido, phenylhydroxyacetamido, phenylacetoxyacetamido, α-oxophenylacetamido, thienylacetamido, benzamido, p-methylbenzamido, p-t-butylbenzamido, p-methoxybenzamido, p-chlorobenzamido, p-bromobenzamido, the groups mentioned in Chapter 7 (pp. 218–287) of Theodora W. Greene, "Protective Groups in Organic Synthesis" (hereinafter referred to briefly as the literature), phenylglycylamido, phenylglycylamido whose amino group is protected, p-hydroxyphenylglycylamido and p-hydroxyphenylglycylamido whose at least one of amino and hydroxyl groups is protected. As the protective group for the amino group of said phenylglycylamido or p-hydroxyphenylglycylamido, the groups mentioned in Chapter 7 (pages 218–287) of the literature, for instance, can be employed. As the protective group for the hydroxyl group of said p-hydroxyphenylglycylamido, the groups mentioned in Chapter 2 (pages 10–72) of the literature, for instance, can be employed.

The lower alkoxy group $R^2$ includes straight- or branched-chain $C_1$–$C_4$ alkoxy groups such as methoxy, ethoxy, n-propoxy, isopropoxy, n-butoxy, isobutoxy, sec-butoxy, tert-butoxy and so on.

The lower acyl group $R^2$ includes straight- or branched-chain $C_1$–$C_4$ acyl groups such as formyl, acetyl, propionyl, butyryl, isobutyryl and so on.

The protective group for the protected hydroxyl group of said lower alkyl group substituted by hydroxy or protected hydroxy, $R^2$, and the protective group for said protected hydroxyl group $R^2$ include, among others, the various groups mentioned in Chapter 2 (pages 10–72) of the literature. The substituted lower alkyl group $R^2$ may be substituted, on the same or different carbon atoms, by the same or different substituent groups selected from among hydroxyl and protected hydroxyl groups such as those mentioned above.

The carboxy-protecting group $R^3$ includes, among others, benzyl, p-methoxybenzyl, p-nitrobenzyl, diphenylmethyl, trichloroethyl, tert-butyl and the groups mentioned in Chapter 5 (pages 152–192) of the literature.

The substituent group by which the aryl group $R^4$ or $R^6$ may be substituted includes, among others, halogen, hydroxy, nitro, cyano, aryl, lower alkyl, amino, mono(lower)alkylamino, di(lower)alkylamino, mercapto, alkylthio or arylthio of the formula $R^8S$— ($R^8$ means a lower alkyl group or an aryl group), formyloxy, acyloxy of the formula $R^8COO$— ($R^8$ is as defined above), formyl, acyl of the formula $R^8CO$— ($R^8$ is as defined above), alkoxy or aryloxy of the formula $R^8O$— ($R^8$ is as defined above), carboxy, and alkoxycarbonyl or aryloxycarbonyl of the formula $R^8OCO$— ($R^8$ is as defined above). The aryl group $R^4$ or $R^6$ may be substituted by one or more substituent groups, which may be the same or different groups selected from among the groups mentioned just above.

The alkenyl of said alkenyl group which may be substituted, $R^5$, includes, among others, vinyl, 1-propenyl, 2-propenyl, 1-butenyl, 2-butenyl, allyl, 1-cyclohexenyl and so on. The alkynyl of said alkynyl group which may be substituted, $R^5$, includes ethynyl, 1-propynyl, 1-butynyl and so on. The nitrogen-containing heteroaromatic group of said nitrogen-containing heteroaromatic group which may be substituted, $R^5$, includes thiazol-2-yl, thiadiazol-2-yl, benzothiazol-2-yl, oxazol-2-yl, benzoxazol-2-yl, imidazol-2-yl, benzimidazol-2-yl, pyrimidinyl, pyridyl and so on. The substituent group which may occur on said alkenyl, alkynyl, aryl or nitrogen-containing heteroaromatic group $R^5$ includes the substituent groups mentioned for $R^4$. The alkenyl, alkynyl, aryl or nitrogen-containing heteroaromatic group $R^5$ may be substituted by one or more substituent groups which may be the same or different groups selected from among the substituent groups mentioned just above.

The substituent group or groups which may occur on the lower alkyl or aryl group $R^7$ include the substituent groups mentioned for $R^4$. The lower alkyl or aryl group $R^7$ may have, either on the same carbon atom or on different carbon atoms, one or more substituent groups, which may be the same or different groups selected from among the substituent groups mentioned above.

The compound of general formula (1) according to the invention can be produced, for example by reacting an azetidinone derivative of general formula (3)

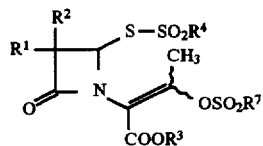
(3)

wherein $R^1$, $R^2$, $R^3$ and $R^4$ are as defined above; $R^7$ represents a fluorine atom, a lower alkyl group which may be substituted or an aryl group which may be substituted, with an organotin compound of general formula (4)

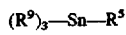
(4)

wherein $R^9$ represents a lower alkyl group; $R^5$ is as defined above, in the presence of a palladium catalyst in a suitable solvent.

The azetidinone derivative of general formula (3), which is used as the starting compound in the invention, can be produced, for example by the process described in Japanese Unexamined Patent Publication No. 165367/86.

As specific examples of the organotin compound of general formula (4) may be mentioned tetraethyltin, tetrabutyltin, vinyltributyltin, (Z)-1-propenyltributyltin, 1-(tributylstannyl)-2-methylprop-1-ene, (trifluorovinyl)tributyltin, 1-(tributylstannyl)-1-propyne, (p-methoxyphenyl)tributyltin, 1-methyl-2-(tributylstannyl)pyrrole, (4-t-butyl-1-cyclohexen-1-yl)trimethyltin, (4-t-butyl-1-cyclohexen-1-yl)tributyltin, (E)-1,2-bis(tributylstannyl)ethylene, [p-(trifluoromethyl)phenyl]tributyltin, 1-methoxy-1-(tributylstannyl)ethylene, aryltributyltin, ethynyltributyltin, (phenylethynyl)tributyltin and so on. The proportion of the organotin compound of general formula (4) relative to the compound of general formula (3) is generally about 1 to about 3 moles and preferably about 1 to about 2 moles.

The palladium catalyst includes, among others, salts of palladium(II) such as palladium acetate, palladium chloride, palladium bromide, palladium iodide, palladium nitrate, palladium sulfate, palladium acetoacetate, palladium oxide, bis(acetonitrile)palladium dichloride, bis(phenylacetonitrile)palladium dichloride, bis(triphenylphosphine)palladium chloride, etc. and palladium (0) compounds such as tetrakis(triphenylphosphine)palladium, tetrakis(tri-2-furylphosphine)palladium, tetrakis(tri-2-thienylphosphine)palladium, tris(dibenzylideneacetonyl)bispalladium, tris(dibenzylideneacetone)dipalladium, bis(dibenzylideneacetone)palladium and so on. The proportion of the palladium catalyst is generally about 0.01 to about 1 mole and preferably about 0.01 to about 0.5 mole to each mole of the azetidinone derivative of general formula (3).

The solvent can be liberally selected from among the known solvents provided that it is capable of dissolving the compound of general formula (3) and inert under the conditions of the reaction. Thus, for example, halogenated hydrocarbons such as dichloromethane, chloroform, dichloroethane, trichloroethane, dibromoethane, propylene dichloride, carbon tetrachloride, freon, etc., cyclic ethers such as tetrahydrofuran, dioxane, etc., nitriles such as acetonitrile, propionitrile, butyronitrile, isobutyronitrile, valeronitrile, etc., amides such as dimethylacetamide, dimethylformamide, N-methylpyrrolidinone, etc., and dimethyl sulfoxide can be mentioned. These solvents can be used singly or in combination. The amount of the solvent is generally about 0.5 to about 200 l and preferably about 1 to about 50 l per kg of the compound of general formula (3).

The above reaction is carried out in the temperature range of generally −60° to 100° C. and preferably −50° to 50° C., and the reaction time is generally about 0.1 to about 24 hours.

The β-lactam compound of general formula (1), thus produced, can be purified by the conventional extraction, crystallization and other procedures to provide a substantially pure product. Of course, other purification procedures can also be employed.

The 2-substituted methyl-3-cephem compound of general formula (2) according to the invention can be produced by permitting a nucleophilic agent of the general formula

(5)

wherein $R^6$ is as defined above; M represents a metal atom, to act upon a β-lactam compound of formula (1) wherein $R^5$ is a vinyl group, that is to say a β-lactam compound of general formula (1a)

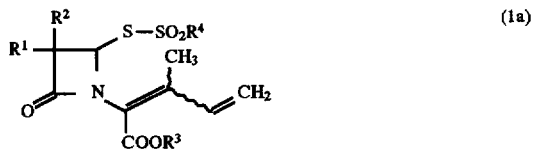
(1a)

wherein $R^1$, $R^2$, $R^3$ and $R^4$ are as defined above, in a suitable organic solvent.

Referring to the above general formula (5), the metal atom designated by M includes, among others, alkali metals such as lithium, sodium and potassium.

The ratio of said nucleophilic agent of general formula (5) to said β-lactam compound of general formula (1a) is generally about 1 to about 3 equivalents and preferably about 1 to about 1.5 equivalents. This reaction is carried out in a suitable organic solvent. The organic solvent mentioned just above can be widely selected from the known solvents provided that it is capable of dissolving the β-lactam compound of general formula (1a) and inert to the very reaction. Thus, lower alkyl esters of lower carboxylic acids, such as methyl formate, ethyl formate, propyl formate, butyl formate, methyl acetate, ethyl acetate, propyl acetate, butyl acetate, methyl propionate, ethyl propionate, etc., ethers such as diethyl ether, ethyl propyl ether, ethyl butyl ether, dipropyl ether, diisopropyl ether, dibutyl ether, methylcellosolve, dimethoxyethane, etc., cyclic ethers such as tetrahydrofuran, dioxane, etc., nitriles such as acetonitrile, propionitrile, butyronitrile, isobutyronitrile, valeronitrile, etc., substituted or unsubstituted aromatic hydrocarbons such as benzene, toluene, xylene, chlorobenzene, anisole, etc., halogenated hydrocarbons such as dichloromethane, chloroform, dichloroethane, propylene dichloride, carbon tetrachloride, etc., aliphatic hydrocarbons such as pentane, hexane, heptane, octane, etc., cycloalkanes such as cyclopentane, cyclohexane, cycloheptane, cyclooctane, etc., amides such as dimethylformamide, dimethylacetamide, etc. and dimethyl sulfoxide can be mentioned as examples. In the invention, these solvents can be used singly or in combination. Moreover, where necessary, the solvent may contain water. The amount of the solvent is generally about 0.5 to about 200 l and preferably about 1 to about 50 l per kg of the compound of general formula (1a). This reaction is conducted in a temperature range of −70° to about 180° C. and preferably −50° to about 120° C. The reaction time is generally about 0.5 to about 30 hours.

The resultant 2-substituted methyl-3-cephem compound of general formula (2) can be subjected to the conventional extraction, crystallization and other procedures following the above reaction to provide a substantially pure compound, although other purification procedures can of course be employed.

The 2-exomethylenecephem compound of general formula (6)

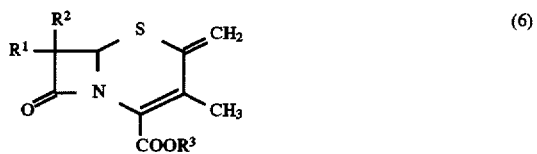

(6)

wherein $R^1$, $R^2$ and $R^3$ are as defined above, can be produced by permitting a base to act upon the above 2-substituted methyl-3-cephem compound of general formula (2). As preferred examples of the base mentioned just above, aliphatic amines and aromatic amines can be mentioned. Among such examples are triethylamine, diisopropylamine, ethyldiisopropylamine, tributylamine, 1,5-diazabicyclo [4.3.0]nonene-5 (DBN), 1,8-diazabicyclo[5.4.0]undecene-7 (DBU), 1,4-diazabicyclo[2.2.2]octane (DABCO), piperidine, N-methyl-piperidine, 2,2,6,6-tetramethylpiperidine, morpholine, N-methylmorpholine, N,N-dimethylaniline, N,N-dimethylaminopyridine and so on. These bases can be used singly or in combination. The proportion of the base relative to the 2-substituted methyl-3-cephem compound of general formula (2) is about 1 to about 10 equivalents and preferably about 1 to about 5 equivalents. This reaction is carried out in a temperature range of −70° to about 180° C. and preferably −50° to about 120° C. The reaction time is generally about 0.1 to about 30 hours.

The invention can be carried into practice by reacting a compound of general formula (1a) with a compound of general formula (5) to produce a 2-substituted methyl-3-cephem compound of general formula (2) and subjecting the reaction mixture as such to the above-mentioned reaction between the cephem compound and base.

Furthermore, particularly when the 2-substituted methyl-3-cephem compound of general formula (2) need not be isolated, it may be so arranged that both the nucleophilic agent of general formula (5) and the base are permitted to act concurrently on the β-lactam compound of general formula (1a) from the beginning of the reaction. In this case, it is sufficient to use the nucleophilic agent in a proportion of generally about 0.001 to about 2.0 equivalents and preferably about 0.001 to about 1.5 equivalents relative to the compound of general formula (1a).

After the reaction, the resultant 2-exomethylenecephem compound of general formula (6) can be subjected to the conventional extraction, recrystallization and other procedures to provide a pure product, although other purification procedures can of course be employed.

BEST MODE OF PRACTICING THE INVENTION

The following examples are intended to describe the invention in further detail.

EXAMPLE 1

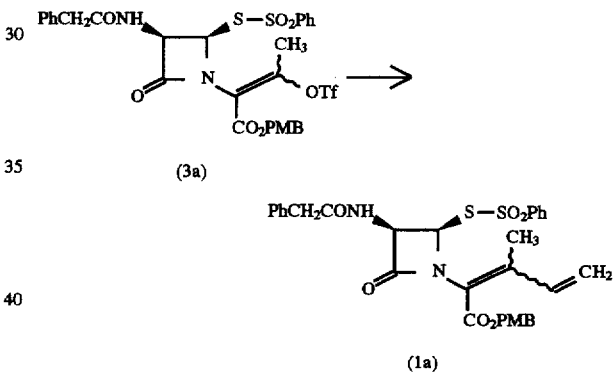

The compound of general formula (3) wherein $R^1$=phenylacetamido, $R^2$=H, $R^3$=p-methoxybenzyl, $R^4$=phenyl, $R^7$=trifluoromethyl (hereinafter referred to as compound (3a)) (100 mg) and palladium acetate (6.1 mg) were weighed and dried under reduced pressure, followed by nitrogen purging. To this mixture was added N-methylpyrrolidinone (1 ml) to prepare a homogeneous solution. Then, vinyltributyltin (60 μl) was added and the mixture was stirred at room temperature for 12 hours. The reaction mixture was then transferred to a separatory funnel using ethyl acetate and washed with water and saturated NaCl—$H_2O$. The extract was dried ($Na_2SO_4$) and concentrated to provide a crude product. This product was then purified by column chromatography to provide a compound of general formula (1) wherein $R^1$=phenylacetamido, $R^2$=H, $R^3$=p-methoxybenzyl, $R^4$=phenyl, $R^5$=vinyl [hereinafter referred to as compound (1a)] (59.7 mg, yield 72%).

NMR ($CDCl_3$): δ ppm; 2.05 (s, 3H), 3.66 (ABq, 2H, J=16.7 Hz), 3.81 (s, 3H), 4.71 (dd, 1H, J=7.3 Hz, 5.4 Hz), 5.03 & 5.16 (ABq, 2H, J=11.9 Hz), 5.49 (d, 1H, J=11.3 Hz), 5.64 (d, 1H, J=17.3 Hz), 5.81 (d, 1H, J=5.4 Hz), 5.92 (d, 1H, J=7.3 Hz), 7.52 (dd, 1H, J=17.3 Hz, 11.3 Hz), 6.90–7.74 (m, 14H)

EXAMPLE 2

The reaction procedure of Example 1 was repeated using 2-propenyltributyltin in lieu of vinyltributyltin for 22 hours to provide a compound of general formula (1) wherein $R^1$=phenylacetamido, $R^2$=H, $R^3$=p-methoxybenzyl, $R^4$=phenyl, $R^5$=2-propenyl [hereinafter referred to as compound (1b)] in a yield of 50%.

NMR (CDCl$_3$): δ ppm; 1.78 (d, 3H, J=1.5 Hz), 2.06 (s, 3H), 3.60 & 3.64 (ABq, 2H, J=17.7 Hz), 3.80 (s, 3H), 4.58 (d, 1H, J=1.5 Hz), 4.76 (dd, 1H, J=1.5 Hz, 1.5 Hz), 4.86 (dd, 1H, J=7.4 Hz, 5.2 Hz), 4.99 & 5.04 (ABq, 2H, J=11.9 Hz), 5.83 (d, 1H, 5.2 Hz), 5.99 (d, 1H, J=7.4 Hz, NH), 6.87–7.76 (m, 14H)

EXAMPLE 3

The reaction procedure of Example 1 was repeated using 2-methyl-1-propenyltributyltin in lieu of vinyltributyltin for 24 hours to provide a compound of general formula (1) wherein $R^1$=phenylacetamido, $R^2$=H, $R^3$=p-methoxybenzyl, $R^4$=phenyl, $R^5$=2-methyl-1-propenyl [hereinafter referred to as compound (1c)] in a yield of 20%.

NMR (CDCl$_3$): δ ppm; 1.57 (s, 3H), 1.74 (s, 3H), 2.06 (s, 3H), 3.58 & 3.65 (ABq, 2H, J=22.0 Hz), 3.81 (s, 3H), 4.81 (dd, 1H, J=7.2 Hz, 5.2 Hz), 4.97 & 5.10 (ABq, 2H, J=11.9 Hz), 5.83 (d, 1H, 5.2 Hz), 5.91 (d, 1H, J=7.2 Hz), 6.09 (s, 1H), 6.98–7.73 (m, 14H)

EXAMPLE 4

The reaction procedure of Example 3 was repeated using tris(dibenzylideneacetone) dipalladium in lieu of palladium acetate for 24 hours to provide the compound (1c) in a yield of 67%. The NMR spectrum of this product was in complete agreement with that of the compound (1c) obtained in Example 3.

EXAMPLE 5

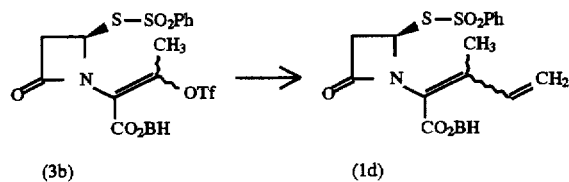

(3b)    (1d)

To a mixture of the compound of general formula (3) wherein $R^1$=$R^2$=H, $R^3$=diphenylmethyl, $R^4$=phenyl, $R^7$=trifluoromethyl [hereinafter referred to as compound (3b)] (391 mg) and palladium acetate (27.4 mg) was added N-methylpyrrolidinone (4 ml) and, after stirring, vinyltributyltin (268 μl) was added. The mixture was stirred at room temperature for 1 hour, after which it was extracted with ethyl acetate-aqueous potassium fluoride solution and, then, washed with water. The extract was dried over sodium sulfate and the solvent was distilled off under reduced pressure. The residue was purified by column chromatography to provide a compound of general formula (1) wherein $R^1$=$R^2$=H, $R^3$=diphenylmethyl, $R^4$=phenyl, $R^5$=vinyl [hereinafter referred to as compound (1d)] (250 mg, yield 79%).

NMR (CDCl$_3$): δ ppm; 1.92 (s, 3H), 3.01 (dd, 1H, J=2.8 Hz, 15.9 Hz), 3.52 (dd, 1H, J=5.6 Hz, 15.9 Hz), 5.49 (dd, 1H, J=0.9 Hz, 12.1 Hz), 5.58 (dd, 1H, J=2.8 Hz, 5.6 Hz), 5.64 (dd, 1H, J=0.9 Hz, 16.2 Hz), 6.93 (s, 1H), 7.25–7.63 (m, 16H)

EXAMPLE 6

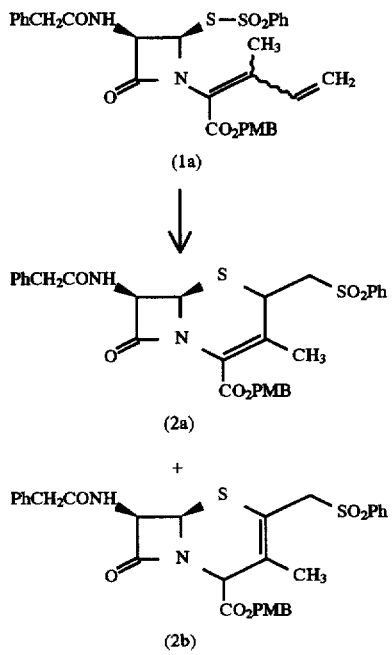

Compound (1a) (50 mg) and sodium benzenesulfinate (13.5 mg) were weighed and dried under reduced pressure, followed by nitrogen purging. To this mixture was added dimethylformamide (1 ml) and the mixture was stirred to prepare a homogeneous solution. The solution was further stirred at room temperature for 1.5 hours. The reaction mixture was then transferred to a separatory funnel using ethyl acetate and washed with water and saturated NaCl—H$_2$O. The extract was then dried (Na$_2$SO$_4$) and concentrated to provide a crude product. This product was purified by column chromatography to provide the Δ$^3$ compound of general formula (2) wherein $R^1$=phenylacetamido, $R^2$=H, $R^3$=p-methoxybenzyl, $R^6$=phenyl [hereinafter referred to as compound (2a)] (38.1 mg, yield 81%) and the Δ$^2$ compound of general formula (2) wherein $R^1$=phenylacetamido, $R^2$=H, $R^3$=p-methoxybenzyl, $R^6$=phenyl [hereinafter referred to as compound (2b)] (8.7 mg, yield 12%).

Compound (2a): NMR (CDCl$_3$): δ ppm; 2.03 (s, 3H), 3.33 (dd, 1H, J=14.8 Hz, 8.4 Hz), 3.39 (dd, 1H, J=11.3 Hz, 2.8 Hz), 3.57 & 3.62 (ABq, 2H, J=16.3 Hz), 3.80 (s, 3H), 3.88 (dd, 1H, J=8.4 Hz, 2.8 Hz), 4.76 (d, 1H, J=4.7 Hz), 5.14 & 5.17 (ABq, 2H, J=11.9 Hz), 5.82 (dd, 1H, J=9.1 Hz, 4.7 Hz), 5.88 (d, 1H, J=9.1 Hz), 6.85–7.93 (m, 14H), Compound (2b): NMR (CDCl$_3$): δ ppm; 1.37 (s, 3H), 3.66 (s, 2H), 3.81 (s, 3H), 3.81 & 3.98 (ABq, 2H, J=14.8 Hz), 4.71 (s, 1H, CH), 5.08 & 5.14 (ABq, 2H, J=11.9 Hz), 5.20 (d, 1H, J=4.0 Hz), 5.75 (dd, 1H, J=9.8 Hz, 4.0 Hz), 7.00 (d, 1H, J=9.8 Hz), 6.86–7.82 (m, 14H)

EXAMPLE 7

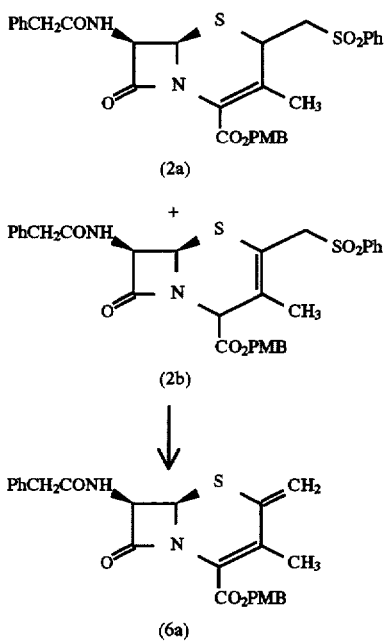

The mixture (100 mg) of compound (2a) and compound (2b) was weighed and dried under reduced pressure, followed by nitrogen purging. This mixture was dissolved in dimethylformamide (1 ml) followed by addition of 1,8-diazabicyclo[5.4.0]undecene-7 (DBU) (26 μl) and the mixture was stirred at room temperature for 10 minutes. This reaction mixture was transferred to a separatory funnel using ethyl acetate and washed with water and saturated NaCl—$H_2O$. The extract was then dried ($Na_2SO_4$) and concentrated to provide a crude product. This crude product was purified by column chromatography to provide a compound of general formula (6) wherein $R^1$=phenylacetamido, $R^2$=H, $R^3$=p-methoxybenzyl [hereinafter referred to as compound (6a)] (65.4 mg, yield 86%).

NMR ($CDCl_3$): δ ppm; 2.18 (s, 3H), 3.62 & 3.67 (ABq, 2H, J=16.2 Hz), 3.81 (s, 3H), 5.02 (d, 1H, J=4.6 Hz), 5.18 & 5.21 (ABq, 2H, J=11.8 Hz), 5.58 (s, 1H), 5.78 (dd, 1H, J=8.9 Hz, 4.6 Hz), 5.81 (s, 1H), 6.06 (d, 1H, J=8.9 Hz), 6.86–7.40 (m, 9H)

EXAMPLE 8

The reaction procedure of Example 7 was repeated using diisopropylethylamine in lieu of 1,8-diazabicyclo[5.4.0]undecene-7 (DBU) as the base for 24 hours to provide the compound (6a) in a yield of 88%. The NMR spectrum of this product was in complete agreement with that of the compound obtained in Example 7.

EXAMPLE 9

The reaction procedure of Example 7 was repeated using triethylamine in lieu of 1,8-diazabicyclo[5.4.0]undecene-7 (DBU) as the base for 20 hours to provide the compound (6a) in a yield of 68%. The NMR spectrum of this product was in complete agreement with that of the compound obtained in Example 7.

EXAMPLE 10

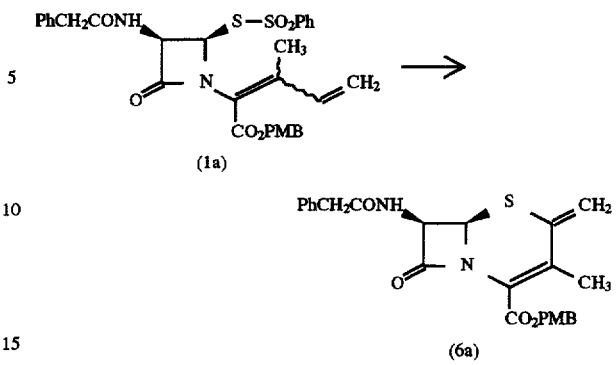

Compound (1a) (50 mg) was weighed and dried under reduced pressure, followed by nitrogen purging. To this was added toluene (0.5 ml) to prepare a homogeneous solution. Then, sodium benzenesulfinate (1.3 mg) and 1,8-diazabicyclo[5.4.0]undecene-7 (DBU) (15 μl) were added in the order mentioned and the mixture was stirred at room temperature for 1.5 hours. This reaction mixture was transferred to a separatory funnel using ethyl acetate and washed with water and saturated NaCl—$H_2O$. The extract was then dried ($Na_2SO_4$) and concentrated to provide a crude product. This product was purified by column chromatography to provide compound (6a) (26.4 mg, 70%). The NMR spectrum of this product was in complete agreement with that of the compound obtained in Example 7.

EXAMPLE 11

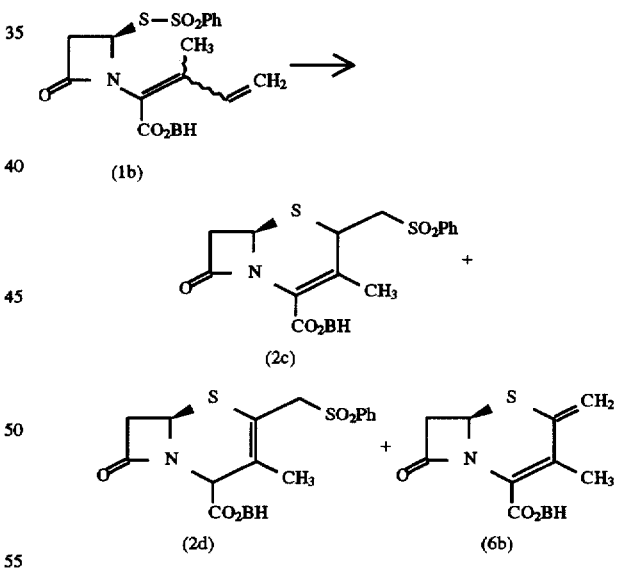

Compound (1b) (1.22 g) and sodium benzenesulfinate (520 mg) were weighed and stirred with dimethylformamide (13 ml). The stirring was continued for 80 minutes, at the end of which time the solution was extracted using ethyl acetate-water. The organic layer was washed with water twice and dried over sodium sulfate. The solvent was then distilled off under reduced pressure and the residue was purified by column chromatography to provide a mixture (1.09 g, 89%) of the $\Delta^3$ compound of general formula (2) wherein $R^1$=$R^2$=H, $R^3$=diphenylmethyl, $R^6$=phenyl [hereinafter referred to as compound (2c)] and the $\Delta^2$ compound of general formula (2) wherein $R^1=R^2=H$, $R^3$=diphenylmethyl, $R^6$=phenyl [hereinafter referred to as compound (2d)] and a compound of general formula (6) wherein $R^1=R^2=H$, $R^3$=diphenylmethyl [hereinafter referred to as compound (6b)] (91.4 mg, 10%).

Compound (2c): NMR (CDCl$_3$): δ ppm; 1.90 (s, 3H), 2.93 (dd, 1H, J=2.2 Hz, 15.7 Hz), 3.34 & 3.43 (ABq, 2H, J=14.0 Hz), 3.41 (s, 2H), 3.58 (dd, 1H, J=5.0 Hz, 15.7 Hz), 3.83 (d, 1H, J=4.6 Hz, SCH)+3.86 (d, 1H, J=5.2 Hz, SCH), 4.56 (dd, 1H, J=2.2 Hz, 5.0 Hz), 6.96 (s, 1H), 7.22–7.96 (m, 15H)

Compound (2d): NMR (CDCl$_3$): δ ppm; 1.71 (s, 3H), 2.84 (dd, 1H, J=1.2 Hz, 14.6 Hz), 3.44 (dd, 1H, J=4.1 Hz, 14.6 Hz), 3.83, 4.07 (ABq, 2H, J=14.6 Hz), 4.82 (s, 1H), 4.83 (dd, 1H, J=1.2 Hz, 4.1 Hz), 6.87 (s, 1H), 7.22–7.96 (m, 15H)

Compound (6b): NMR (CDCl$_3$): δ ppm; 2.07 (s, 3H), 2.97 (dd, 1H, J=2.2 Hz, 15.6 Hz), 3.59 (dd, 1H, J=4.8 Hz, 15.6 Hz), 4.80 (dd, 1H, J=2.2 Hz, 4.8 Hz), 5.53 (s, 1H), 5.74 (s, 1H), 7.02 (s, 1H), 7.25–7.48 (m, 10H)

EXAMPLE 12

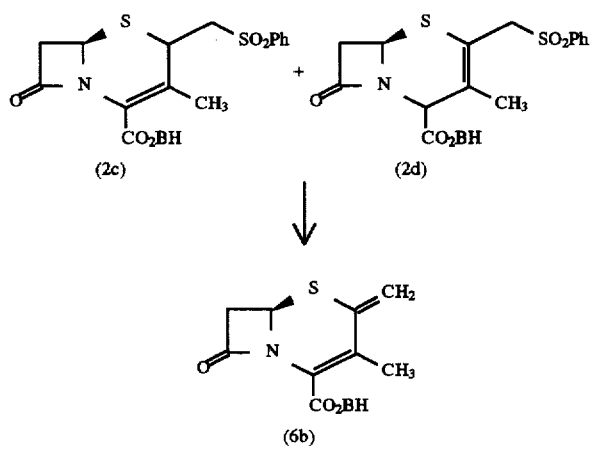

The mixture (23.9 mg) of compound (2c) and compound (2d) was weighed and stirred with dimethylformamide (0.3 ml). Then, at room temperature, diisopropylethylamine (32.0 μl) was added and the mixture was stirred for 85 minutes. The reaction mixture was then extracted using ethyl acetate-water and the extract was washed with water twice and dried over sodium sulfate. The solvent was then distilled off under reduced pressure and the residue was purified by column chromatography to provide compound (6b) (12.5 mg, 72%). The NMR spectrum of this compound was in complete agreement with the compound (6b) obtained in Example 11.

EXAMPLE 13

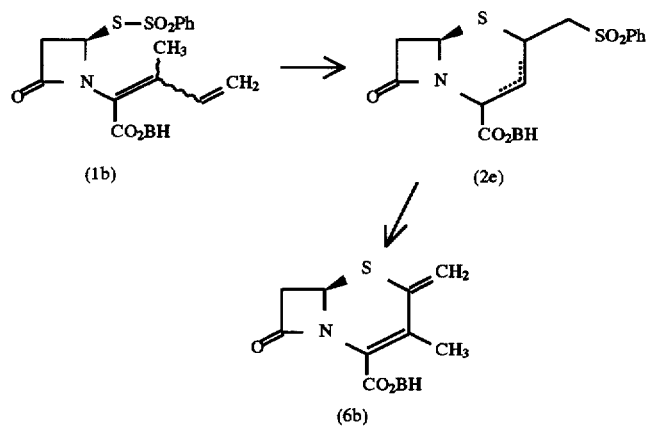

Compound (1b) (30.4 mg) and sodium benzenesulfinate (12 mg) were weighed and stirred with dimethylformamide (0.3 ml). The mixture was stirred for 1 hour, at the end of which time it was extracted using ethyl acetate-water. The extract was washed with water twice and dried over sodium sulfate. The solvent was then distilled off under reduced pressure and the residue was directly subjected to the next reaction. Thus, the residue was stirred with dimethylformamide (0.3 ml) and, then, diisopropylethylamine (40.8 μl) was added at room temperature. The mixture was stirred at room temperature for 2 hours, after which it was extracted using ethyl acetate-water. The extract was washed with water twice and dried over sodium sulfate. The solvent was then distilled off under reduced pressure and the residue was purified by column chromatography to provide compound (6b) (17.8 mg, 81%). The NMR spectrum of this product compound was in complete agreement with that of the compound (6b) obtained in Example 11.

INDUSTRIAL APPLICABILITY

The β-lactam compound of general formula (1) and 2-substituted methyl-3-cephem compound according to the present invention are of value as intermediates for the synthesis of penam, penem and cephem antibiotics.

What is claimed is:

1. A β-lactam compound of the formula wherein $R^1$ represents a hydrogen atom, a halogen atom, an amino group or a protected amino group; $R^2$ represents a hydrogen atom, a halogen atom, a lower alkoxy group, a lower acyl group, a lower alkyl group, a lower alkyl group substituted by a hydroxyl or protected hydroxyl group, a hydroxyl group or a protected hydroxyl group; $R^1$ and $R^2$ taken together represent =O; $R^3$ represents a hydrogen atom or a carboxyl-protecting group; $R^4$ represents an aryl group optionally having at least one substituent selected from the group consisting of halogen, hydroxy, nitro, cyano, aryl, lower alkyl, amino, mono(lower)alkylamino, di(lower) alkylamino, mercapto, $R^8S-$, formyloxy, $R^8COO-$, formyl, $R^8CO-$, $R^8O-$, carboxy and $R^8OCO-$; wherein $R^8$ is a lower alkyl group or an aryl group; and $R^5$ represents a vinyl group.

* * * * *

UNITED STATES PATENT AND TRADEMARK OFFICE
CERTIFICATE OF CORRECTION

PATENT NO.: 5,693,792
DATED : December 2, 1997
INVENTOR(S): TORII et al.

It is certified that an error appears in the above-identified patent and that said Letters Patent is hereby corrected as shown below:

On the cover page, item [73], in the assignee's name, "Otsuga" should read --Otsuka--

Signed and Sealed this

Twenty-ninth Day of February, 2000

*Attest:*

Q. TODD DICKINSON

*Attesting Officer*     *Commissioner of Patents and Trademarks*